US010655122B2

(12) United States Patent
Kubicek et al.

(10) Patent No.: US 10,655,122 B2
(45) Date of Patent: May 19, 2020

(54) METHOD, LYSIS SOLUTION AND KIT FOR SELECTIVELY DEPLETING ANIMAL NUCLEIC ACIDS IN A SAMPLE (71) Applicant: QIAGEN GmbH, Hilden (DE)

(72) Inventors: Johann Kubicek, Köln (DE); Thorsten Singer, Solingen (DE); Antje-Katrin Sander, Hünxe (DE); Eva Hänssler, Leverkusen (DE); Dominic O'Neil, Hilden (DE)

(73) Assignee: QIAGEN GMBH, Hilden (DE)

(*) Notice: Subject to any disclaimer, the term of this patent is extended or adjusted under 35 U.S.C. 154(b) by 0 days.

(21) Appl. No.: 15/568,098

(22) PCT Filed: Apr. 20, 2015

(86) PCT No.: PCT/EP2015/058497
§ 371 (c)(1),
(2) Date: Oct. 20, 2017

(87) PCT Pub. No.: WO2016/169579
PCT Pub. Date: Oct. 27, 2016

(65) Prior Publication Data
US 2018/0142231 A1    May 24, 2018

(51) Int. Cl.
C12Q 1/6806    (2018.01)
C12N 1/06    (2006.01)
C12N 15/10    (2006.01)
C12N 9/22    (2006.01)

(52) U.S. Cl.
CPC .......... C12N 15/1003 (2013.01); C12N 9/22 (2013.01); C12Q 1/6806 (2013.01); C12Q 2521/301 (2013.01); C12Q 2521/537 (2013.01); C12Q 2523/113 (2013.01)

(58) Field of Classification Search
None
See application file for complete search history.

(56) References Cited

U.S. PATENT DOCUMENTS 7,893,251 B2 *  2/2011  Lorenz .................. C12N 9/22
                                                       536/25.4
2014/0154687 A1 *  6/2014  Talebpour .......... C12Q 1/6848
                                                       435/6.12
2017/0152510 A1 *  6/2017  Lorenz ............... C12N 15/1017

FOREIGN PATENT DOCUMENTS

| DE | 10-2005-009479 A1 | 9/2006 |
| WO | WO-2006/092278 A1 | 9/2006 |
| WO | WO-2009/015484 A1 | 2/2009 |
| WO | WO-2011/061274 A1 | 5/2011 |
| WO | WO-2011/070507 A1 | 6/2011 |
| WO | WO-2013/003376 A2 | 1/2013 |
| WO | WO-2015/062699 A1 | 5/2015 |

OTHER PUBLICATIONS

Benzonase Nuclease. 1999. Novagen, pp. 1-4. (Year: 1999).*
International Search Report in International Application No. PCT/EP2015/058497, filed Apr. 20, 2015.
McCann et al, "Evaluation of MolYsis™ Complete5 DNA extraction method of detecting Staphylococcus aureus DNA from whole blood in a sepsis model using PCR/pyrosequencing", Journal of Microbiological Methods, Feb. 3, 2014, pp. 1-7, vol. 99, Amsterdam, NL.
Horz Et All, "Selective isolation of bacterial DNA from human clinical specimens", Journal of Microbiological Methods, Nov. 28, 2007, pp. 98-102, vol. 72, Amsterdam, NL.
"Molecular Sepsis Diagnostics; Research Products and CE IVD Products, Chapter 2: MolYsis—Pre-analytic Kits for Bacterial DNA Isolation", Molzym GmbH & Co. KG, 2009, pp. 1-40, Internet Citation, Bremen, DE.
"Selective Enrichment of Bacterial and Fungal DNA", Molzym GmbH & Co. KG, Sep. 26, 2014, Bremen, DE.

* cited by examiner

Primary Examiner — Channing S Mahatan
(74) Attorney, Agent, or Firm — Saliwanchik, Lloyd & Eisenschenk (57) ABSTRACT The present invention relates to a method for selectively depleting animal nucleic acids from non-animal nucleic acids in a sample, which comprises animal cells and at least one further type of cells, selected from microbial cells and plant cells or a combination thereof, to a lysis solution A to be used in and to a kit to carry out said method as well as to the use of a particular silica membrane as both, a filtration matrix for separating essentially intact microbial and/or plant cells from lysed animal cells and an adsorption matrix for nucleic acids, in particular in a method according to the present invention.

15 Claims, 6 Drawing Sheets

METHOD, LYSIS SOLUTION AND KIT FOR SELECTIVELY DEPLETING ANIMAL NUCLEIC ACIDS IN A SAMPLE

CROSS-REFERENCE TO RELATED APPLICATIONS

This application is the U.S. national stage application of International Patent Application No. PCT/EP2015/058497, filed Apr. 20, 2015, the disclosure of which is incorporated herein by reference in its entirety.

The present invention relates to a method for selectively depleting animal nucleic acids from non-animal nucleic acids in a sample, which comprises animal cells and at least one further type of cells, selected from microbial cells and plant cells or a combination thereof, to a lysis solution A to be used in and to a kit to carry out said method as well as to the use of a particular silica membrane as both, a filtration matrix for separating essentially intact microbial and/or plant cells from lysed animal cells and an adsorption matrix for nucleic acids, in particular in a method according to the present invention.

Microbial cells, i.e. cells of microorganisms such as bacteria, archae and fungi, including yeast, or a combination thereof, usually are encountered in combination with animal cells in biological samples, such as for example animal body fluids. The accurate and quick detection of pathogenic microorganisms in such samples is of utmost importance for a fast and accurate diagnosis and hence therapy. This is in particular true since many infections caused by microorganisms are still associated with high morbidity and mortality, despite of advances in current treatment methods. Thus, a selective depletion of animal cells and, with respect to biomolecular methods based on the analysis of nucleic acids, animal nucleic acids, from non-animal cells and nucleic acids, respectively, is desirable for both, conventional analysis and/or culturing techniques for microbial and/or plant cells as well as analysis of their nucleic acids.

However, while conventional culturing techniques usually tolerate a rather large amount of animal "background", i.e. cells, cell debris and/or former intracellular compounds released from the animal cells, the animal background should be as low as possible in methods of analyzing the non-animal nucleic acids. This is particular true e.g. for whole genome amplification (WGA) or the so-called next generation sequencing (NGS).

Using conventional culturing techniques often several days are required to identify a microorganism. Besides that only known organisms or organisms able to grow on the specific media can be detected. This means it is impossible to analyze or characterize a complete microbiome. For this reason, nowadays methods based on the amplification of microbial nucleic acid are used for detecting microorganisms. Herein, usually a pathogenic microorganism is first isolated from a sample, e.g. a human blood sample, lysed and then its nucleic acids are amplified using primers specific for the pathogenic microorganism to be detected. Of course, this is only possible if it is already known which type of pathogenic microorganism shall be detected.

In recent years, methods have been developed to amplify and sequence nucleic acids without the need for specific primers, known for example as whole genome amplification (WGA), whole transcriptome amplification (WTA) or whole nucleic acid amplification (WNA) followed by next generation sequencing. Said methods are known by the persons skilled in the art and are described in the literature. However, as these methods do not employ a specific primer, virtually all nucleic acids present in a sample are amplified and/or sequenced.

While a human cell usually comprises about 6 to 9 picograms genomic DNA and 1 mL blood comprises about 4 to 10 million white blood cells, an *E. coli* cell usually contains only about 5 femtograms of DNA. In addition, the number of microbial cells in samples of infected patients usually is much lower than the content of their own cells. For instance, the ratio of microbial to human DNA in blood samples of patients with sepsis usually is in the range of about 1 to $2\times10^9$. For this reason, several methods have been developed in the state of the art to (more or less) selectively deplete animal cells and/or animal nucleic acids in such samples.

Methods and kits dedicated to the problem of selectively depleting animal cells/animal nucleic acids from microbial cells/microbial nucleic acids are described for example in WO 2006/092278 A1, WO 2009/015484 A1, WO 2011/070507 A1, WO 2011/061274 A1 and/or are commercially available under the trademark names VYOO kit (SIRS-Lab, Jena, Germany), MolYsis kit (Molzym GmbH & Co. KG, Bremen, Germany) or QIAamp® UCP PurePathogen Blood kit (QIAGEN, Hilden, Germany).

Using the VYOO kit, both animal as well as microbial cells present in the sample are lysed in a first step, and the total DNA present in the sample is then isolated. In a further step the microbial DNA is enriched using an antibody-functionalized solid phase which selectively binds the non-methylated microbial DNA, while the methylated human DNA is not bound to said solid phase and thus can be separated from the microbial DNA. In further steps, the microbial DNA has to be eluted from the solid phase and has to be precipitated from the eluate, which makes this method rather time-consuming. In addition, usually neither binding of the microbial cells to the antibody-functionalized solid phase nor the subsequent precipitation from the eluate is quantitative, so that significant amounts of microbial DNA might be lost.

The methods described in WO 2006/092278 A1, WO 2009/015484 A1, WO 2011/070507 A1 and WO 2011/061274 A1 on the other hand employ specific lysis buffers to selectively lyse higher eukaryotic cells in the presence of microbial cells, the latter remaining essentially intact during said lysis step. The lysed animal cells are then separated from the essentially intact microbial cells by means of several washing and centrifugation steps. This, however, may be very time-consuming in many instances as well. In addition, the highly alkaline lysis buffer employed in WO 2011/070507 A1 (pH≥9.5) and the chaotropic buffers employed in WO 2011/061274 A1, WO 2006/092278 A1 and the MolYsis kit might not be suitable for sensitive samples or employ toxic substances, respectively.

In addition to the above mentioned drawbacks of the methods and kits known in the state of the art, the ratio of a microbial DNA to animal DNA in samples isolated and purified using these methods and kits often is only about 1:1000 or even lower and thus still is too low for next generation sequencing, as in this case 99.99% of the resources and costs would be spent on (known) animal DNA fragments.

It was therefore an object of the present invention to provide a method and a kit for selectively depleting animal nucleic acids from non-animal nucleic acids in a sample which comprises animal cells and at least one further type of cells, selected from microbial cells and plant cells or a combination thereof, which allows a significant reduction of animal nucleic acids in the sample in comparison to the methods and kits known in the state of the art.

This object is met by the method, lysis solution and kit of the present invention. Using the method, lysis solution and/or kit of the present invention it is possible to significantly reduce the amount of animal cells and in particular animal nucleic acids in a sample (initially) comprising both animal as well as microbial and/or plant cells. For instance, it is possible to obtain a relative amount of microbial and/or plant nucleic acids, respectively, e.g. DNA, as high as at least 50%, 60%, 70%, 75%, 80%, 85%, 90%, 92.5%, 95%, 97.5%, 98%, 98.2% or even higher, based on the total amount of nucleic acids according to PCR in a processed sample, which initially, i.e. before commencing the method of the present invention, may have comprised a ratio of microbial and/or plant nucleic acids to animal nucleic acids of about $1:10^5$ or even less. This makes the method, lysis solution and kit particularly suitable for isolating nucleic acids which are intended to be used in subsequent methods like WGA, WNA, WTA and/or NGS.

In addition, even though the method of the present invention is not limited to the use of the lysis solution of the present invention as described herein, using said specifically adapted lysis solution the above mentioned drawbacks associated with lysis buffers of highly alkaline pH or those employing chaotropic substances can be avoided as well.

Further, using the method of the present invention, the number of laborious and time-consuming centrifugation steps may be reduced significantly, which steps in addition always carry the risk of sample loss.

Thus, the present invention relates to a method for selectively depleting animal nucleic acids from non-animal nucleic acids in a sample, comprising animal cells and at least one further type of cells, selected from microbial cells and plant cells or a combination thereof, comprising the steps of:
i) essentially selectively lysing the animal cells by contacting the sample with a lysis solution A to obtain a mixture comprising the essentially intact microbial cells and/or plant cells as well as the animal nucleic acids released from the lysed animal cells into solution,
iii) digesting both, DNA and RNA, of the animal nucleic acids in the presence of the essentially intact microbial and/or plant cells,
v) essentially separating the microbial and/or plant cells from the liquid part of the sample, including the digested animal nucleic acids.

In the present invention the term "selectively depleting" is to be understood as reducing the amount of animal nucleic acids present in the sample so that the ratio of animal nucleic acids to non-animal nucleic acids in the sample is shifted in favor of the non-animal nucleic acids. Preferably, the amount of animal nucleic acids in the sample is reduced by a factor of at least $10^3$, more preferably at least $10^4$, even more preferably $10^5$ and most preferably at least $5 \times 10^5$ or even higher, calculated as the amount of animal nucleic acid (both intra-as well as extracellular) initially being present in the sample, i.e. before commencing the method of the present invention, divided by the amount of animal nucleic acids present in the sample after selectively depleting the animal nucleic acids according to the method of the present invention. Preferably, the amount of non-animal nucleic acids in the sample obtained after completing the method of the present invention which originates from the at least one further type of cells initially being present in the sample, is at least 50%, 60%, 70%, 75%, 80%, 85%, 90%, 92.5%, 95%, 97.5%, 98%, 98.2% or even higher, based on the total amount of nucleic acids in the processed sample.

If not particularly otherwise defined the term "essentially" shall be understood in a way that in any case more than 50% of the considered trait is obtained, preferably at least 60%, more preferably at least 70%, even more preferably at least 75%, 80%, 85%, 90%, or 95% and most preferably at least 98%. "Essentially" can also represent 100%. The term "substantially" shall be understood in similar way.

In terms of the present invention animal nucleic acids include both single- as well as double-stranded nucleic acids from animal cells, including ribonucleic acids (RNA) and deoxyribonucleic acids (DNA), such as, but not limited to mRNA, miRNA, tRNA, rRNA, snRNA, gDNA, plasmid DNA, and mtDNA (mitochondrial DNA).

Animal cells are eukaryotic cells which, in contrast to e.g. plant cells, lack chloroplast and cell walls. Herein the term "animal cells" includes both cell types being present in "organized" structures, such as for example tissues or cell cultures, as well as isolated and/or single cells, for instance being present in body fluids or excrements of a mammal and in particular a human, including for example blood, cerebrospinal fluid, urine, feces and the like.

The term "animal cells" shall comprise in particular mammalian cells, but further insect cells, bird cells, poultry cells, fish cells, amphibian cells, reptilian cells, molluscan cells, wherein mammal cells are preferred and human cells are particularly preferred.

In terms of the present invention non-animal nucleic acids include both single- as well as double-stranded RNA and DNA of microbial and/or plant origin, such as, but not limited to mRNA, miRNA, tRNA, rRNA, snRNA, plasmids, gDNA, plasmid DNA, and mtDNA (mitochondrial DNA).

"Microbial cells" are cells of a microorganism, i.e. an organism that either consists of one single cell (unicellular organism) or cell clusters including biofilms. In terms of the present invention microorganisms include both prokaryotes as well as eukaryotes, such as bacteria, fungi, yeast, microscopic algae, archae and protozoa. The microbial and/or plant cells may stem from a naturally occurring or a genetically engineered organism.

Plant cells are eukaryotic cells which, in contrast to animal cells, comprise a cell wall. In contrast to the cell walls of bacteria and fungi the cell wall of a plant usually comprises cellulose, hemi-cellulose, pectin and often lignin.

In the present invention the microbial cells preferably may be selected from the group comprising bacteria, archae and fungi, including yeast, or a combination of the aforementioned cell types. Even more preferably the microbial cells include bacterial cells and most preferably essentially may represent bacterial cells. This means, that most preferably the amount of bacterial cells with respect to the total number of non-animal cells present in the sample after using the inventive method may be at least 90%, 95%, 98%, 99% or even higher.

In terms of the present invention "bacteria" may include both, gram-positive as well as gram-negative bacteria, in particular bacteria which are known to be involved in the development of a sepsis in animals, in particular in humans. Examples of bacteria species of particular interest are *Mycobacterium* spp., *Enterococcus, Enterobacter, Klebsiella, Proteus, Pseudomonas, Serratia, Escherichia, Acinetobacter, Streptococcus, Staphylococcus, Salmonella, Legionella, Chlamydia, Shigella, Pseudomonas, Listeria, Yersinia, Corynebacterium, Bordetella, Bacillus, Clostridium, Haemophilus, Helicobacter* and *Vibrio*, wherein the bacteria often involved in sepsis are in particular *Staphylococcus*

*aureus, Escherichia coli, Streptococcus viridans, Streptococcus pneumoniae, Streptococcus faecalis* and/or species of *Klebsiella, Enterobacter, Serratia* and *Pseudomonas.*

Preferred fungi cells may represent or originate from cells of the species *Aspergillus, Basidiobolus, Cephalosporium, Skopulariopsis, Rhizomucor, Entomophthora, Mucor, Syncephalastrum, Absidia, Altenaria, Rhizopus, Stemphylium, Nigrospora, Chrysosporium, Botrytis, Helmithosporium, Curvularia, Hemispora, Phoma, Paecilomyces* and *Thielavia,* in particular *A. fumigatus, A. tereus, A. niger, A. nidulans, A. homegadus, A. flavus B. microsporus, B. rhanarum, C. crysogenum, C. corebiobides, C. regatum* and *C. diospyri.*

The microbial cells may represent yeast cells as well, in particular of pathogenic yeasts of the species *Candida,* e.g. *C. tropicalis, C. glabrata, C. krusei, C. parapsilosis, C. albicans, C. guilliermondii,* as well as algae cells, e.g. of *Euglena* spp., *Coscinodiscus* spp., *Trachelomonas* spp., *Gymnodinium sanguineum, Dinophysis nitra, Ceratium massiliense, Chlorella, Chlorococcum* or *Eremosphaera,* or from protozoa, e.g. *Plasmodium, Trypanosoma, Leishmania, Toxoplasma* and *Cryptosporidium,* preferably *Plasmodium malariae, Plasmodium falciparum, Trypanosoma brucei, Trypanosoma cruzei, Toxoplasma gondii, Cryptosporidium parvum, Cryptosporidium serpentis* and *Cryptosporidium hominis.*

The sample processed in the method of the present invention preferably may comprise or be derived from tissue, tissue homogenates, cell cultures, bone marrow aspirates, bone homogenates, swabs, swab rinsates or body fluids, preferably body fluids, more preferably body fluids being selected from the group comprising amniotic fluid, aqueous humor, bile, bladder lavage, blood, including whole blood, blood samples stabilized by citrate, EDTA, heparin or the like or blood concentrates such as concentrates of thrombocytes or erythrocytes, blood plasma, breast exudates, bronchoalveolar lavage, cerebrospinal fluid, chyle, chyme, cytosol, feces, gastric contents, interstitial fluid, joint fluid, lymph, menses, mucus, plasma, pleural fluid, pus, saliva, sebum, semen, serum, sputum, sweat, synovial fluid, tears, urine, vaginal secretions and vitreous humour.

The sample preferably may be derived from its natural environment, in particular an animal, preferred a animal organism. It may be particularly preferred that the sample represents a body fluid of a mammal, in particular a human, or a concentrate thereof or a diluted body fluid. In addition, suspensions or slurries of samples in an aqueous solution, for example a buffer, may be suitable as a sample to be processed in the method of the present invention.

The sample volume is not particularly limited. For example, sample volumes ranging from 1 μL to 1 L, preferred 100 μL to 500 mL, more preferred 200 μL to 100 mL and particularly preferred 1 mL to 10 mL may be processed using the method of the present invention.

In terms of the present invention the term "essentially selectively lysing" is used to indicate that preferably 90%, 95%, 98%, 99%, 99.2%, 99.5%, 99.8%, 99.95% or even more of the animal cells initially being present in the sample before carrying out step i) of the method of the present invention are lysed in said step i), while the microbial cells and/or plant cells remain essentially intact. Herein, the term "essentially intact" is used to indicate that at least 90%, 95%, 98%, 99%, 99.2%, 99.5%, 99.8%, 99.95% or even more of said cells, based on the total number of said cells being present in the sample before carrying step i), are not lysed in said step.

In the present invention the term "essentially separating" is used to indicate that at least 80%, 85%, 90%, 95%, 98%, 99%, 99.2%, 99.5%, 99.8%, 99.95% (v/v) or even more of any liquid being present in the sample before step v), including any residual digested animal nucleic acids adhering on or to the essentially intact microbial and/or plant cells is separated from said microbial and/or plant cells in step v).

The method of the present invention combines a step of selectively lysing animal cells in the presence of microbial and/or plant cells, a subsequent step of digesting both, animal DNA as well as animal RNA and a step of fast and reliably separating the essentially intact microbial and/or plant cells from any extracellular liquid part of the sample, including former intracellular compounds of animal cells, such as for example the digested animal nucleic acids.

Using the method of the present invention samples can be obtained, comprising at least 50%, 60%, 70%, 75%, 80%, 85%, 90%, 92.5%, 95%, 97.5%, 98%, 98.2% or even more of microbial and/or plant nucleic acids originally comprised in the sample from samples previously having a ratio of animal DNA to microbial and/or plant DNA in the range of about $10^5$:1, without the need for highly alkaline and/or chaotropic buffers, as demonstrated by the examples included herein.

The method comprises several particularly preferred embodiments. In one embodiment the separation of the microbial and/or plant cells in step (v) are separated from the remaining liquid part of the sample by centrifugation. This is particularly suitable when samples are treated comprising not too much animal cells, but several microbial/plant cells, e.g. a ratio of animal cells:microbial/plant cells of $10^3$:1, or $10^2$:1. Such samples are e.g. buccal swabs, liquor, plasma, amniotic fluid, aqueous humour, bile, bladder lavage, blood plasma, breast exudates, bronchoalveolar lavage, cerebrospinal fluid, chyle, cytosol, feces, gastric contents, in particular gastric acid, interstitial fluid, joint fluid, lymph, mucus, plasma, pleural fluid, saliva, sebum, serum, sputum, sweat, synovial fluid, tears, urine, vaginal secretions and vitreous humour, without being restricted to said samples. Independent therefrom this might be also particularly suitable if the microbial cells/plant cells are difficult to open by chemical/enzymatic treatment and therefore the cell lysis of the microbial/plant cells has to be supported mechanically, e.g. by the usage of glass beads or a similar tool.

In another preferred embodiment, if samples are treated having a high amount of animal cells compared to the number of microbial cells/plant cells, e.g. a ratio of $10^6$:1 or higher, like whole blood, tissue, tissue homogenates, cell cultures, bone marrow aspirates, bone homogenates, blood products, blood samples stabilized by citrate, EDTA, heparin or the like or blood concentrates such as concentrates of thrombocytes or erythrocytes, semen or similar samples, without being restricted the the mentioned, it might be advantageous to separate the microbial cells/plant cells from the remainder of the lysed animals cells and the liquid part of the sample by filtration. Independent from the ratio of animal cells to microbial/plant cells in the sample the filtering may also be used instead of centrifugation, if the microbial cells of interest may be suitably lysed by chemical or enzymatic lysis without the need of any mechanical support.

As in this embodiment of the method of the present invention mainly relies on a step of filtering the sample for separating the microbial and/or plant cells from any remaining liquid part of the sample, including lysed animal cells, animal cell debris and/or digested animal nucleic acids, laborious and time-consuming steps of washing and separating microbial and/or plant cells by means of centrifugation can be avoided.

If the separation of the microbial/plant cells is carried out by centrifugation, said centrifugation preferably is carried out by applying a force of less than 40,000×g, preferably of less than or equal to 30,000×g, more preferably of less than or equal to 20,000×g and even more preferably of less than or equal to 15,000×g and preferably of more than or equal to 1,000×g, more preferably of more than or equal to 2,000×g, even more preferably of more than or equal to 3,500×g and most preferably of more than or equal to 5,000×g. Centrifugation of the sample in the range of from 6,000×g to 12,000, in particular from 7,000 to 10,000×g is particularly preferred. After the separation by a first centrifugal step the pellet might by washed at least one with an adequate washing buffer, followed by a further pelleting of the cells by centrifugation, before the microbial/plant cells are lysed for further analysis of their content.

In the embodiment of separation via filtration preferably step v) comprises filtering the sample through a solid filter to essentially retain the microbial and/or plant cells as retentate on the filter while the liquid part of the sample, including the digested animal nucleic acids, essentially passes the filter as filtrate.

In terms of the present invention a "solid filter" includes any filter made of solid material, including surface as well as depth filters. A surface filter acts more or less like a solid sieve and keeps the particles to be retained, here being microbial and/or plant cells, on its surface. A depth filter on the other hand is a bed of porous material which retains the particles throughout the medium as they pass said medium and may be made of a membrane, monolithic or granual material or a combination thereof. The filter used in the method of the present invention may as well comprise both, a surface filter as well as a depth filter.

The filter used in the method of the present invention comprises at least one part having a pore size being in the range of 0.1-1.5 µm, preferably 0.2-1.0 µm, more preferred 0.3-0.8 µm (particularly preferred 0.25+/−0.05-0.8 µm) and most preferred 0.5-0.7 µm.

The filter used in step v) for separating the microbial and/or plant cells from the liquid part of the sample preferably may comprise polyester, polyethersulfone (PES), cellulose, cellulose acetate (CA), mixed cellulose esters (MCE), polytetrafluoroethylene (PTFE), polyamide (PA), Nylon, polypropylene (PP), ceramics, glass fibers, silica or combinations or mixtures thereof as a filtering material.

Preferably the flow through the filter may be supported by applying pressure to the feed side of the filter or vacuum to the filtrate side or even more preferably by centrifuging the filter placed in a suitable centrifuging vessel, preferably at a force in the range of about 5,000 to 15,000×g, more preferably of about 8,000 to about 12,000×g and most preferably of about 10,000×g for a time period being in the range of from about 30 s to 30 min, preferably of about 1 min to about 20 min, even more preferably of about 5 min to about 15 min and most preferably of about 10 min. Filtration preferably may be carried out at about room temperature (20±5° C.).

As already mentioned above, the filter used in the method of the present invention is may combine both, a surface as well as a depth filter. For example, filtering units such as spin columns may be used, which comprise an upper surface filter, for example a filter having a pore size of about 0.25 µm made of for example cellulose acetate, followed by a depth filter comprising a glass fiber filter comprising pores of the above mentioned pore size.

In step iii) preferably both, DNA and RNA, of the animal nucleic acids may be digested in one step, preferably enzymatically, more preferably by an endonuclease which degrades both, DNA and RNA.

In terms of the present invention DNA as well as RNA of the animal nucleic acids is digested in one step, if both DNA as well as RNA is degraded at the same time. This may be done chemically, enzymatically, or by any other method suitable to degrade DNA and RNA of animal origin while leaving microbial and/or plant cells essentially intact. Preferably, the animal nucleic acids are digested enzymatically by the action of one or more nucleases. It is for example possible to add both a DNase as well as an RNase to the sample in step iii) (or vice versa, i.e. the sample to a solution comprising these enzymes). More preferably, a nuclease is employed which degrades both DNA as well as RNA, in particular an endonuclease which degrades both DNA as well as RNA. Preferred may be enzymes which are effective at pH below 9.5 and in particular at an almost neutral pH (pH 6.0-8.0). In particular for sensitive samples it may also be desirable to use an enzyme which not only is effective at 37° C., but also at room temperature (20±5° C.) or even below. When employing nucleases of high specific activity towards nucleic acids, e.g. preferably of at least $10^4$ U/mg, more preferably of at least $10^5$ U/mg, a smaller amount of these nucleases has to be added to the sample. This minimizes any efforts which have to be undertaken to remove the nuclease(s) after completing step iii).

The step of digesting the animal nucleic acids preferably is carried at a temperature in the range of from about 10° C. to about 50° C., preferably of from about room temperature (20±5° C.) to about 37° C., for a time period being in the range of from about 5 min to 3 hours, preferably of from about 10 min to about 2 hours, more preferably of from about 15 min to about 1 hour and most preferably for about 30 min.

Further, it is preferred to use nucleases which attack all kinds of nucleic acids, including single and double-stranded, linear as well as circular DNA and RNA. Preferably, the nuclease(s) digest(s) the nucleic acids to monophosphate terminated oligonucleotides of less than 50 bases in length, preferably of less than 20 bases in length, more preferably less than 15 bases in length, even more preferably less than 10 bases in length, still even more preferably less than 8 bases in length and most preferably less than 6 bases in length. Fragments of this size can easily be separated from the remaining cells by filtration using one or more of the filters described above, without the risk of clogging the filter and/or enhancing the viscosity of the sample to be filtered.

A suitable endonuclease is for example the genetically engineered endonuclease produced in *E. coli* strain W3110, containing the proprietary pNUC 1 plasmid, as described in U.S. Pat. No. 5,173,418 and in EP 0229 866 B1, Benzonase®, available by Merck, Germany, Cyanase™, available by RiboSolutions, USA or Pierce™ universal nuclease, available by Thermo Scientific, Germany, without being restricted to the mentioned.

In principle both, endonucleases, i.e. enzymes cleaving the phosphodiester bond within a polynucleotide chain, and exonucleases, cleaving phosphodiester bond at the end of a polynucleotide chain, may be used. The use of one or more endonucleases may be preferred.

In principle a broad range of different lysis buffers or lysis solutions for selectively lysing animal cells in the presence of microbial and/or plant cells (referred to as "lysis solution" in the following) may be used in step i) in the method of the present invention. For environmental and safety reasons the use of an essentially chaotrop-free lysis solution A may be preferred.

Chaotropic substances denature proteins, increase the solubility of non-polar substances in water and destroy hydrophobic interactions. In addition, they also mediate the binding of nucleic acids to solid phases such as silica membranes or glass particles. Chaotropic ions comprise commonly iodide, perchlorate, (iso)thiocyanate and/or guanidinium ions. Accordingly, the lysis solution used in the method of the present invention as well as the lysis solution A of the present invention preferably are essentially free from iodide, perchlorate, (iso)thiocyanate and/or guanidinium ions.

In terms of the present invention the lysis solution A is essentially chaotrop-free, if it contains less than 2 M, preferably less than 1 M, more preferably less than 0.1 M, even more preferably less than 0.01 M, still even more preferably less than 0.001 M and most preferably none of the above mentioned chaotropic substances at all.

Preferably the lysis solution A used in step i) comprises at least one surfactant, a water soluble salt and/or a viscosity modifier, and further optionally a polyanionic sulfonate, as described in detail in the following.

Preferably the lysis solution A may comprise at least one surfactant, more preferably at least one non-ionic surfactant. It may be preferred that all surfactants being present in the lysis solution A are non-ionic surfactants.

The non-ionic surfactants preferably may be selected from the group comprising sorbitan esters of fatty acids, polyoxyethylene sorbitan esters of fatty acids, polyoxyalkylene ethers of fatty alcohols, polyoxyalkylene ethers of alkylphenols, poloxamers, saponins or mixtures thereof.

Poloxamers are non-ionic triblock copolymers composed of an essential hydrophobic chain of polyoxypropylene flanked by two hydrophilic chains of polyoxyethylene and are commercially available for example from BASF (Ludwigshafen, Germany).

The lysis solution A preferably comprises at least one saponin. Saponins are amphipathic glycosids of steroids, steroid alkaloids or triterpenes. Being secondary metabolites, they can be isolated from natural sources, in particular fruits, roots, tubers, leafs and the like of plants, for example the fruits of *Sapindus* (soap nuts). Purified plant extracts comprising saponins are commercially available for example from Sigma-Aldrich (Saint Louis, Mo., USA) or from AppliChem (Darmstadt, Germany). It may be further preferred that any non-ionic surfactant being present in the lysis solution A represents a saponin.

The above mentioned surfactants, in particular the saponins preferably may be present in the lysis solution A in a total amount of from about about 0.01 to about 15% (w/v), based on the whole lysis solution A, preferably in an amount of from 0.1 to 14%, more preferably in an amount of from 1 to 13%, even more preferably of from about 2 to about 12%, even more preferably of from about 4 to 10% and most preferably of from about 5 to 8%. The mentioned amounts refer to the total amount of the included surfactants.

Furthermore, the lysis solution A may optionally comprise a polyanionic sulfonate, preferably sodium polyanethol sulfonate. The polyanionic sulfonate may be present in a concentration of from 0.001 to 50 mM, preferably of from 0.01 to 10 mM, more preferably of from 0.1 to 5 mM, even more preferably of from 0.5 to 3 mM and most preferably of from 1.0 to 2.0 mM, based on the whole lysis solution A.

Furthermore, the lysis solution A may comprise a water-soluble salt which preferably may be selected from the group comprising water-soluble acetates, sulfates, glutamates or mixtures thereof, for example their sodium salts or a mixture thereof. Acetates and glutamates or a mixture thereof are particularly preferred. The water-soluble salt(s) preferably may be present in a total amount ranging of from 10 to 1,000 mM, preferably of from 50 to 850 mM, more preferably of from 100 to 500 mM and most preferably of from 160 to 250 mM, based on the whole lysis solution A.

Furthermore, the lysis solution A may comprise a viscosity modifier to increase or decrease the viscosity of the lysis solution A and optionally any solution to which the lysis solution A is added. The viscosity modifier preferably may be selected from the group comprising sugars, more preferably from the group comprising glucose and/or sucrose. The viscosity modifying agent preferably may be present in an amount ranging of from 10 to 1.000 mM, preferably of from 100 to 900 mM, more preferably of from 300 to 700 mM and most preferably of from 400 to 500 mM, based on the whole lysis solution A.

The pH of the lysis solution A preferably may be in the range of from 4 to 9, more preferably of from 4.5 to 8.5 and most preferably of from 5 to 8.

The lysis solution A preferably may comprise a combination of the aforementioned substances as well, and may for example represent an essentially chaotrop-free lysis solution A comprising or consisting of at least one surfactant, preferably at least one saponin and either of i) a water-soluble salt and a viscosity modifier, ii) a polyanionic sulfonate and a viscosity modifier, iii) a polyanionic sulfonate and a water-soluble salt, or iv) a polyanionic sulfonate, a water-soluble salt and a viscosity modifier, all of the aforementioned substances preferably being selected from the groups already described in more detail above.

The lysis solution A preferably comprises at least one saponin, a water soluble acetate and/or glutamate salt and sucrose and/or glucose as a viscosity modifier in the above mentioned concentrations. In a particular preferred embodiment the lysis solution A comprises at least one saponin, a glutamate salt and sucrose, or may consist of these ingredients and water.

Dependent from the treated sample and from the desired analysis steps carried out with the microbial/plant cells or with any biomolecules isolated from the microbial/plant cells it might be preferable to include a polyanionic sulfonate as mentioned above into the lysis solution A, or not. E.g. for blood samples, in particular for blood samples of blood cultures, it might be preferred to include such a polyanionic sulfonate, since said compound has a positive effect on the stability of microbial cells in such samples. Thus, said cells are maintained during the treatment to isolate them. Cells isolated by such a method can be well analyzed and determined e.g. by further culturing. On the other hand, polyanionic sulfonates are known to have a negative effect in e.g. PCR analysis due to their inhibition of the PCR amplification. Since the compound is very difficult to remove, it might be advantageous to keep any polyanionic sulfonate out from the lysis solution A, if analysis later on is based on PCR, in particular, if in step (v) the microbial/plant cells are separated from the liquid remainder by centrifugation.

Thus, it is preferred to use a lysis solution A without any polyanionic sulfonate if at least one of the following conditions is fulfilled:

(a) samples are used having a low amount of animal cells (i.e. samples having less than $1 \times 10^6$ cells/ml, preferably less than $10^5$ cells/ml, more preferred less than $10^4$ cells/ml, even more preferred less than $10^3$ cells/ml), e.g. buccal swabs, liquor, plasma, amniotic fluid, aqueous humour, bile, bladder lavage, blood plasma, breast exudates, bronchoalveolar lavage, cerebrospinal fluid, chyle, cytosol, feces, gastric contents, in particular gastric acid, interstitial fluid, joint fluid, lymph, mucus, plasma, pleural fluid, saliva, sebum, serum, sputum, sweat, synovial fluid, tears, urine, vaginal secretions and vitreous humour, without being restricted to said samples;
(b) the microbial/plant cells are separated from the remainder of the lysed animal cells and/or the liquid part of the sample in step (v) by centrifugation;
(c) the content of the microbial cells/plant cells, in particular the nucleic acids isolated from said cells shall be analysed by PCR or a similar reaction.

On the other hand it is preferred to use a lysis solution A comprising a polyanionic sulfonate when at least one of the following conditions is fulfilled:
(d) samples are used having a high amount of animal cells (i.e. samples having at least $1 \times 10^6$ cells/ml, preferably at least $10^7$ cells/ml, more preferred at least $10^7$ cells/ml, even more preferred at least $10^9$ cells/ml), e.g. whole blood, tissue, tissue homogenates, cell cultures, bone marrow aspirates, bone homogenates, blood products, blood samples stabilized by citrate, EDTA, heparin or the like or blood concentrates such as concentrates of thrombocytes or erythrocytes, semen or similar samples, without being restricted the the mentioned;
(e) the microbial/plant cells are separated from the remainder of the lysed animal cells and/or the liquid part of the sample in step (v) by filtration;
(f) the microbial cells or plant cells shall be analysed by further cultivation.

It is particularly pointed out that it is not restrictive or absolutely necessary for the present invention that the lysis solution A comprising a polyanionic sulfonate is used when at least one of the conditions (d), (e) or (f) is present, or using the lysis solution A without any polyanionic sulfonate when at least one of the conditions (a), (b) or (c) is present. However, it might be preferred due to the increased suitability for analysis methods. It might be further preferred that the respective solution is used, if at least two of the mentioned conditions or even all three conditions are fulfilled.

The lysis solution A may be added to the sample in an amount so that the ratio of the sample to the lysis solution A is 10:1 to 1:10, preferably 5:1 to 1:5, further preferred 2:1 to 1:2, wherein a ratio of about 1:1 or exactly 1:1 is particularly preferred. The amount of the lysis solution to be added preferably is calculated dependent from the desired final concentration of the ingredients in the sample for lysis. Thus, if the lysis solution comprises the above described ingredients in a concentration at the upper end as noted above, the ratio of lysis solution:sample may be below 1, whereas said ratio increases above 1, when the lysis solution concentration is more at the lower end of the ranges cited above for each of the ingredients. The preferred final concentration of the ingredients in the sample after addition of the lysis solution is preferably represented by the half of the concentrations, respectively, as cited above or below for the lysis solution.

In addition to the already described essential steps i), iii) and v) the method of the present invention further may comprise the additional steps of: ii) essentially removing the liquid part of the sample from the remaining cells, and/or iv) removing and/or inactivating any nuclease present along with the remaining cells, preferably by digesting it with a proteinase.

It may be preferred that both steps ii) and iv) are carried out in the method of the present invention, wherein the numbering indicates the preferred order of steps.

Regarding step ii) it may be preferred to essentially remove the liquid part of the sample from the essentially intact microbial and/or plant cells after selective lysis of the animal cells according to step i) of the method of present invention, before digesting any animal nucleic acids still being present along with the microbial and/or plant cells, for example adhering to them. In terms of the present invention the liquid part of the sample is essentially removed, if at least 90%, preferably at least 95%, more preferably at least 97%, even more preferably at least 98%, still even more preferably at least 99% and most preferably at least 99.5% (v/v) of the liquid part of the sample being present after step i) is removed during step ii) before step iii) is carried out. This may for example be done by filtering and/or centrifuging the sample to obtain a cell pellet/a cell retentate on the filter comprising the microbial and/or plant cells and aspirating, decanting and/or pipetting off the liquid supernatant filtrates, without being limited to this.

In principle, any method suitable for removing a liquid from essentially intact microbial and/or plant cells without compromising the integrity of said cells is suitable. It may be preferred to use a spin column equipped with a suitable filter, as described in more detail below to essentially remove the liquid part of the sample form the remaining cells by filtration with the aid of a centrifugal force. Centrifuging preferably may be carried out at a force in the range of about from 5,000 to 15,000×g, more preferably of from 8,000 to 12,000×g and most preferably of about 10,000×g, preferably for about 2 to 20 min, more preferably for about 5 to 15 min and most preferably for about 10 min. Surprisingly it has been found that even when processing rather small amounts of microbial and/or plant cells, e.g. of about $10^5$ to $10^6$ *E. coli* cells in a 1 mL blood sample, centrifuging during step ii) preferably may be carried out in a round-bottom vessel to obtain a cell pellet, which both can be easily separated from the remaining supernatant and has a structure which assures an efficient digesting of any remaining animal nucleic acids which adhere to the microbial and/or plant cells. In this respect, remarkably better results are achieved using a round-bottom centrifuging vessel than using a conical-bottom vessel.

Regarding step iv), after digesting the animal nucleic acids in the sample the nuclease may be removed and/or inactivated. This may be done after or before essentially separating the microbial and/or plant cells from the liquid part of the sample by filtering the sample according to step v) and preferably may be carried out before said step v). The nuclease(s) may for example be removed by washing the microbial and/or plant cells with water or a suitable aqueous washing buffer and/or by inactivating said nuclease(s), e.g. by digesting it with a proteinase, by adding suitable nuclease inhibitors and/or a heating step. Proteinase digestion, optionally in combination with one or more washing steps, may be preferred for removing and/or inactivating the nuclease(s). Suitable proteinases are for example Proteinase K and/or QIAGEN Protease, both commercially available from QIAGEN (Hilden, Germany).

The enzymatic digestion of the nuclease(s) preferably may be carried out at a temperature in the range of from about 10° C. to 50° C., preferably at a temperature in the range of from about room temperature (20±5° C.) to about 37° C. and most preferably at room temperature, by incubating the sample with the proteinase for about 10 min to 3 hours, preferably for about 15 min to 2 hours, more preferably for about 20 min to about 1 hour and most preferably for about 30 min. In addition, the cell pellet may be loosened up in this enzymatic digestion step, in particular if Proteinase K is used, to ensure a fast rate of filtration without clogging of the filter in the following filtration step v).

The method of the present invention may comprise further steps, for example intermediate washing steps carried out before or after any of steps i), ii), iii), iv) and/or v). It may for example be preferred to wash the isolated microbial and/or plant cells on the surface of the filter obtained after step v) with water or a suitable washing buffer, for example by adding water onto the filter, and centrifuging it at a force in the range of about 5,000 to about 15,000×g, preferably of about 8,000 to 12,000×g and most preferably of about 10,000×g for about 15 s to 15 min, preferably for about 30 s to 10 min, and more preferably for about 1 min to about 5 min.

After essentially separating the microbial and/or plant cells according to step v) and optionally washing them, the method of the present invention preferably may comprise one or more additional steps of further analyzing the microbial and/or plant cells or any part thereof. These additional steps may comprise both, methods carried out on the essentially intact microbial and/or plant cells, such as for example culturing, cytometry, microscopy, immunodetection, spectroscopy and the like, and/or lysing the microbial or plant cells, as well as methods carried out on or more type of intracellular compounds, including RNA, DNA, proteins, metabolites, lipids, glycosides, parts of the cell wall and the like, for example by blotting techniques or microarray analysis, methods which are well known to a person skilled in the art. Preferably, the method of the present invention may comprise one or mare additional steps of amplifying and/or analyzing the microbial and/or plant nucleic acids, preferably by a method selected from the group comprising whole genome amplification (WGA), whole transcriptome amplification (WTA), and whole nucleic acid amplification (WNA) PCR, including real time PCR (qPCR) or reverse transcriptase-PCR (RT-qPCR) and/or sequencing, in particular next generation sequencing, these methods of concentrating, isolating, purifying, amplifying and/or analyzing the microbial and/or plant nucleic acids being carried out after previous lysis of the respective microbial and/or plant cells.

For analyzing intracellular compounds, e.g. nucleic acids of the microbial or plant cells, said cells are lysed by any of the methods known in the art. These methods include chemical and/or enzymatic lysing a well as mechanical lysing or any combination thereof, without limiting the invention.

Buffers, methods and kits for lysing microbial and plant cells and subsequently isolating and purifying the nucleic acids released from these cells are well known to the skilled person and are commercially available for example from QIAGEN (Hilden, Germany). In said steps either DNA or RNA or both types of nucleic acids may be isolated, purified and/or analyzed. Preferably, at least the DNA of the microbial and/or plant cells is isolated, purified, amplified and/or analyzed.

Further it is possible to carry out a further analysis of both, the microbial and/or plant cells and their intracellular compounds, e.g. by splitting the amount of microbial and/or plant cells obtained after essentially separating them by filtering according to step v) of the method of the present invention and optional washing steps. For instance, one fraction of these cells may be cultured while the other fraction may be lysed. As an alternative, the complete amount of cells obtained may be cultured first and then at least a part of the cells obtained after culturing may be lysed.

The analysis of the cells content, in particular of the biomolecules (nucleic acids, proteins, lipids, etc.) may be carried out by any suitable procedure of isolating and analysing said biomolecules known by a skilled person.

For the isolation and purification of nucleic acids from a lysate, solid phases binding said molecules which comprise e.g. glass and/or silica and to which the nucleic acids only bind in the presence of a suitable binding mediating agent/binding buffer are well known to a person skilled in the art. The solid supports include membranes, particles, beads and the like and are commercially available from various companies. Here, binding mainly is based on adsorption of the nucleic acids to the solid phase. Solid phases which only bind nucleic acids in the presence of a suitable binding mediator/binding buffer or under particular conditions are particular useful in the method of the present invention, as their binding behavior can be "triggered" by adding appropriate binding and/or washing buffers. In addition, by using a glass- or silica-based solid phase it is possible to selectively bind either DNA or RNA or both types of nucleic acids in order to isolate and purify either one or both of them, which is described for example in EP 0 743 950 A1. Thus, it may be preferred to use glass or silica comprising solid phases, e.g. membranes, particles or beads, to isolate and purify the microbial and/or plant nucleic acids in the method of the present invention.

If a filtration step is used for essentially separating the microbial and/or plant cells according to step v) of the method of the present invention it is also possible to combine a surface or a depth filter as described above with a solid phase for binding nucleic acids in the presence of an appropriate binding buffer/binding mediator in one device, such as for example a spin column equipped with a silica membrane, covered on its top by a cellulose acetate filter. In said device, the filter and the silica membrane preferably may be arranged in such a way, that ingredients of a sample added to said device first gets into contact with the filter and have to pass said filter before they get into contact with the silica membrane. When applying the sample after step iii) or preferably after step iv), if present, to the device, the essentially intact microbial and/or plant cells are retained on the filter during filtration step v), while any liquid part of the sample, including the digested animal nucleic acids and further dissolved compounds, passes both, the filter as well as the underlying silica membrane if no appropriate binding mediator is present. To ensure a complete removal of any substance adhering to the cells and/or the device, the device may be washed using water or an appropriate washing buffer. The microbial and/or plant cells being present on the filter may then be lysed using an appropriate lysing buffer. Optionally proteinase digestion or any other suitably nuclease inhibition may then take place to inactivate any nucleases being present in the sample. If an appropriate binding mediator/binding buffer suitable for mediating the binding of the desired nucleic acids, such as for example ethanol or isopropanol (96 to 100%), is added to the device before centrifuging said device, the nucleic acids being present in the sample after lysis of the cells of interest are adsorbed to the silica membrane while the rest of the microbial and/or plant lysate passes down the device. Of course as well a suitable lysing/binding buffer can be used as known by persons skilled in the art. The nucleic acids bound to the solid phase may then further be purified by appropriate washing steps, which are well known to a person skilled in the art, before eluting them with an appropriate elution buffer, for example water.

If a silica membrane having a pore size in the range of 0.1 to 1.5 µm, preferably 0.2 to 1.0 µm, more preferred 0.3 to 0.8 µm is used, said silica membrane can even act as both, a filter for separating essentially intact microbial and/or plant cells from lysed animal cells and as an adsorption matrix for the microbial and/or plant nucleic acids. In this case, the use of a separate filter may be omitted.

The present invention therefore further relates to the use of a silica membrane having a pore size in the range of 0.1 to 1.5 µm preferably 0.2 to 1.0 µm, more preferred 0.3 to 0.8 µm, most preferred 0.5 to 0.7 µm which can even act as both, as a filter for separating essentially intact microbial and/or plant cells from lysed animal cells and as an adsorption matrix for nucleic acids, in a method for isolating, purifying, enriching, amplifying and/or analyzing microbial and/or plant nucleic acids from a sample which comprises animal cells and at least one further type of cells, selected from microbial cells and plant cells or a combination thereof. The method for isolating, purifying, enriching, amplifying and/or analyzing microbial and/or plant nucleic acids preferably comprises the method of the present invention.

Further the present inventions refers to the use of a combination of a filter having a pore size in the range of 0.1 to 1.5 µm, preferably 0.2 to 1.0 µm, more preferred 0.3 to 0.8 µm, most preferred 0.5 to 0.7 µm of any material other than silica, preferably a material as defined above for the filter (except silica) with a silica membrane suitable for binding nucleic acids. Said combination of filter and silica membrane preferably are mounted adjacent to each other, preferably within a tubular device, e.g. a spin column.

The silica filter or the combination of the filter and a silica membrane are preferably used in a method as described above for a) retaining the microbial cells or plant cells in step v) and b) binding the nucleic acids delivered from the microbial or plant cells after their lysis.

The use of a silica filter having a suitable pore size or the use of a combination of a filter having a suitable pore size with an adjacent silica membrane within the same device results in the advantage, that in the above described method the microbial or plant cells separated from the animals cell content don't have to be transferred to another container or vessel for further treatment, e.g. for lysis of the cells and nucleic acid isolation. The sample can be processed further in the same device (e.g. spin column), avoiding any lost of material due to transfer steps. Thus, further according to the invention a spin column is provided comprising a silica filter or a combination of a filter and a silica membrane as described above. Said device can suitably used in the method of the present invention.

As already explained above the method of the present invention is not restricted to the use of any specific animal cell lysis buffers. However, the lysis solution A described above is particularly suitable to be used in the method of the present invention for lysing the animal cells. The present invention therefore furthermore relates to a lysis solution A, preferably a lysis solution A for use in step (i) of the method of the present invention, which comprises at least one saponin a water-soluble salt selected from the group comprising acetates, sulfates, glutamates and mixture thereof and a viscosity modifying agent being selected from the group comprising sucrose and glucose or a mixture thereof. Optionally, the lysis solution A comprises a polyanionic sulfonate, preferably if at least one of the conditions (d), (e) or (f) (see page 17, lines 30 ff. and page 18, lines 1 ff.) have to be considered.

The at least one saponin preferably may be present in a total amount ranging of from from 0.01 to 15% (w/v), preferably of from 2 to 12%, more preferably of from 4 to 10% and most preferably of from 5 to 8%, based on the whole lysis solution A.

The polyanionic sulfonate may be present in a concentration of from 0.001 to 50 mM, preferably of from 0.01 to 10 mM, more preferably of from 0.1 to 5 mM, even more preferably of from 0.5 to 3 mM and most preferably of from 1.0 to 2.0 mM, based on the whole lysis solution A. Preferably the polyanionic sulfonate may represent polyanethol sulfonate.

The water-soluble salt preferably may be present in an amount ranging of from 10 to 1.000 mM, preferably of from 50 to 850 mM, more preferably of from 100 to 500 mM and most preferably of from 160 to 250 mM, based on the whole lysis solution A.

The viscosity modifying agent preferably may be present in an amount ranging of from 10 to 1.000 mM, preferably of from 100 to 900 mM, more preferably of from 300 to 700 mM and most preferably of from 400 to 500 mM, based on the whole lysis solution A.

The pH of the lysis solution A preferably may be in the range of from 4 to 9, more preferably of from 4.5 to 8.5 and most preferably of from 5 to 8.

The lysis solution A of the present invention may be provided as a concentrate or a ready-to-use solution. It may be particularly preferred to store the lysis solution A of the present invention in a frozen form.

The present invention refers further to the use of the lysis solution A in a method for selectively lysing animal cells in presence of non-animal cells, wherein said lysis solution A either is free of any polyanionic sulfonate, if at least one of the following conditions is fulfilled:
(a) samples are used having a low amount of animal cells (i.e. samples having less than $1 \times 10^6$ cells/ml, preferably less than $10^5$ cells/ml, more preferred less than $10^4$ cells/ml, even more preferred less than $10^3$ cells/ml), e.g. buccal swabs, liquor, plasma, amniotic fluid, aqueous humour, bile, bladder lavage, blood plasma, breast exudates, bronchoalveolar lavage, cerebrospinal fluid, chyle, cytosol, feces, gastric contents, in particular gastric acid, interstitial fluid, joint fluid, lymph, mucus, plasma, pleural fluid, saliva, sebum, serum, sputum, sweat, synovial fluid, tears, urine, vaginal secretions and vitreous humour, without being restricted to said samples;
(b) the non-animal, preferably microbial/plant cells are separated from the remainder of the lysed animal cells and/or the liquid part of the sample in step (v) by centrifugation;
(c) the content of the microbial cells/plant cells, in particular the nucleic acids isolated from said cells shall be analysed by PCR or a similar reaction; or
the lysis solution A comprising a polyanionic sulfonate when at least one of the following conditions is fulfilled:
(d) samples are used having a high amount of animal cells (i.e. samples having at least $1 \times 10^6$ cells/ml, preferably at least $10^7$ cells/ml, more preferred at least $10^7$ cells/ml, even more preferred at least $10^9$ cells/nil), e.g. whole blood, tissue, tissue homogenates, cell cultures, bone marrow aspirates, bone homogenates, blood products, blood samples stabilized by citrate, EDTA, heparin or the like or blood concentrates such as concentrates of thrombocytes or erythrocytes, semen or similar samples, without being restricted the the mentioned;
(e) the microbial/plant cells are separated from the remainder of the lysed animal cells and/or the liquid part of the sample in step (v) by filtration;
(f) the microbial cells or plant cells shall be analysed by further cultivation.

The invention furthermore relates to a kit for selectively depleting animal nucleic acids from a sample comprising animal cells and microbial and/or plant cells, preferably by the method of the present invention, comprising at least two of the following components:

(i) a lysis solution for selectively lysing the animal cells in the presence of microbial and/or plant cells, said buffer having a pH in the range of from 4.0 to 9.0,
(ii) an endonuclease capable of degrading both, RNA as well as DNA, or a mixture of at least one DNase and at least one RNase, and/or
(iii) a filter for essentially separating essentially intact microbial and/or plant cells from the liquid part of the sample, including digested animal nucleic acids, by essentially retaining the microbial and/or plant cells while the liquid part of the sample passes the filter as a filtrate.

It is particularly preferred that the kit comprises at least components (i) and (iii). Preferred lysis solutions, endonucleases and filters have already been described above.

The kit further may comprise at least one of the following components: instructions for using the kit (may also be provided on a web-site or any other suitable publication platform), chromatographic means for purifying, concentrating and/or isolating microbial and/or plant cells or nucleic acids, agents or buffers for lysing the microbial and/or plant cells, binding mediators or binding buffers, washing buffers, elution buffers, further means for filtering and/or centrifuging the sample or a combination thereof.

The method, lysis solution A and kit of the present invention are particularly suitable for selectively depleting animal nucleic acids from non-animal nucleic acids of both, gram-positive as well as gram-negative bacteria and outperform the kits presently known for this purpose as demonstrated by the following examples. Thus, the method, lysis solution and kit of the present invention are useful in numerous fields, including for example diagnosing and monitoring of infectious diseases, detection of biological warfare and food inspection, without being limited to this.

LIST OF FIGURES

FIG. 3 shows the CT values obtained in rt-PCR of nucleic acids from blood samples stabilized with different stabilizing agents (lanes I: heparin; lanes II: EDTA; lanes III: citrate; lane IV: water as NTC) and spiked with 1×10$^6$ cells of *Streptococcus haemolyticus* before being processed according to the method of the present invention. Samples shown in the respective lanes a) were processed according to the method of the present invention immediately after being collected and spiked with the cells. Samples shown in the respective lanes b) were stored at room temperature for two days before being processed. Samples shown in the respective lanes c) were stored at room temperature for six days before being processed. Samples shown in the respective lanes d) were stored at 4° C. for two days before being processed. Samples shown in the respective lanes e) were stored at 4° C. for six days before being processed (example 3).

EXAMPLES

General Protocol A for Processing e.g. a Blood Sample According to the Method of the Present Invention 1 mL of the respective blood sample was pipetted into a 2 mL round-bottom Eppendorf tube already containing 500 µL of an lysis solution A according to the present invention and mixed by pulse-vortexing. The mixture was incubated at room temperature for 30 min on a end-over-end shaker. As an animal lysis buffer any suitable lysis buffer can be used. The lysis solution A used in the examples comprised 7.73 wt-% of saponin, 0.19 M of L-glutamic acid monosodium salt monohydrate, 0.48 M sucrose and 1.92 mM polyanethol sulfonic acid sodium salt.

The mixture was then spun for 10 min at 10,000×g in a centrifuge at room temperature. The supernatant was discarded.

600 µL of a buffer comprising 50 mM Tris pH 7.5, 1.5 mM MgCl$_2$ and 20 mM NaCl, and 8 µL of an enzyme mix (DNAse/RNAse and/or restriction enzymes) or a suitable amount of an endonuclease (e.g. Benzoase®, available by Merck, Germany, Cyanase®, available by RiboSolutions, USA, or Pierce™ Universal nuclease, available by Thermo Scientific, Germany) were added to the pellet. The resulting mixture was mixed by pulse-vortexing. The tube was briefly spun in a centrifuge to remove drops from the inside of the lid and then incubated at 37° C. for 30 min with shaking (600 rpm) in a heating block or at room temperature in an end-over-end shaker.

Then 40 µL of Proteinase K (QIAGEN, Hilden, Germany) were added and the sample was mixed by pulse-vortexing. After briefly spinning the tube in a centrifuge to remove drops from the inside of the lid the sample was incubated at room temperature for 30 min in an end-over-end shaker. To remove drops from the inside of the lid the tube was spun for about 5 min.

The samples were then either carefully applied onto a spin column equipped with a filter having a pore size of 0.25+/−0.05 µm, the spin column was placed in an appropriate vessel and spun in a centrifuge at 10,000×g for 3 min at room temperature and the filtrate was discarded; or the samples were spun in a centrifuge at 10,000×g for 15 min to pellet the bacterial cells present in the sample. The pellet might be washed once to three times with PBS.

At this time it is possible to collect the essentially intact non-animal cells from the filter. If lysis of the non-animal cells and subsequent analysis of the non-animal nucleic acids is desired, the following additional steps are carried out:

When a filter was used, for washing the cells 600 µL of water were applied onto the filter and the spin column comprising said filter was spun in a centrifuge at 10,000×g for 3 min at room temperature. The filtrate was discarded.

180 µL of the above mentioned lysis solution A, now supplemented with 20 g/L Lysozyme, were added onto the filter and the filter was incubated at 37° C. for 30 min with shaking at 600 rpm in a heating block.

200 µL of buffer AL (QIAGEN, Hilden, Germany), supplemented with 20 µL of Proteinase K (QIAGEN, Hilden, Germany), were added to the spin column which was then incubated at 56° C. for 30 min with shaking at 600 rpm in a heating block.

To isolate the non-animal nucleic acids by adsorption to a silica membrane, 200 µL ethanol (96-100%) were added to the sample and mixed by pulse-vortexing for 15 s. The sample was then applied onto a silica membrane suitable for nucleic acid binding, for example a silica membrane contained in the spin columns commercially available under the trademark name QIAamp or MinElute by QIAGEN, Hilden, Germany, and processed according to the manufacturer's protocol.

General Protocol B for Processing e.g. a Buccal Swab Sample According to the Method of the Present Invention Coplan FLOQ swabs were used to sample oral (buccal) mucosa cells and then each swab was swirled in 1 mL PBS. Bacteria were directly added to the sample to circumvent irregularies due to differences in washing efficiency. Approximatly $1\times10^4$ or $1\times10^6$ cells were used per sample depending on the according experiment. To have homogenous sample material, several swab samples were combined and the cell suspension was then split up between several samples.

1 mL of the respective sample was pipetted into a 2 mL round-bottom Eppendorf tube already containing 500 µL of a lysis solution A according to the present invention and mixed by pulse-vortexing. The mixture was incubated at room temperature for 30 min on a end-over-end shaker. As an animal lysis buffer any suitable lysis buffer can be used. The lysis solution A used in the examples comprised 7.73 wt-% of saponin, 0.19 M of L-glutamic acid monosodium salt monohydrate, 0.48 M sucrose and optionally 1.92 mM polyanethol sulfonic acid sodium salt, if present.

The mixture was then spun for 10 min at 10,000×g in a centrifuge at room temperature. The supernatant was discarded.

600 µL of a buffer comprising 50 mM Tris pH 7.5, 1.5 mM $MgCl_2$ and 20 mM NaCl, and 8 µL of an enzyme mix (DNAse/RNAse and/or restriction enzymes) or a suitable amount of an endonuclease (e.g. Benzoase®, available by Merck, Germany, Cyanase®, available by RiboSolutions, USA, or Pierce™ Universal nuclease, available by Thermo Scientific, Germany) were added to the pellet. The resulting mixture was mixed by pulse-vortexing. The tube was briefly spun in a centrifuge to remove drops from the inside of the lid and then incubated at 37° C. for 30 min with shaking (600 rpm) in a heating block or at room temperature in an end-over-end shaker.

Then 40 µL of Proteinase K (QIAGEN, Hilden, Germany) were added and the sample was mixed by pulse-vortexing.

After briefly spinning the tube in a centrifuge to remove drops from the inside of the lid the sample was incubated at room temperature for 30 min in an end-over-end shaker. To remove drops from the inside of the lid the tube was spun for about 5 min.

The samples were then either carefully applied onto a spin column equipped with a filter having a pore size of 0.25+/−0.05 µm, the spin column was placed in an appropriate vessel and spun in a centrifuge at 10,000×g for 3 min at room temperature and the filtrate was discarded; or the samples were spun in a centrifuge at 10,000×g for 15 min to pellet the bacterial cells present in the sample. The pellet might be washed once to three times with PBS.

At this time it is possible to collect the essentially intact non-animal cells from the filter or of the pellet. If lysis of the non-animal cells and subsequent analysis of the non-animal nucleic acids is desired, the following additional steps are carried out:

When the microbial cells were separated by filtration, the cells of the filter may be either lysed as described above in Protocol A, or they may be resuspended in 200 µl of lysis buffer ATL and treated as described below for the pellet after centrifugation.

The pellets of the samples after centrifugation were resuspended in 200 µl of lysis buffer ATL (QIAGEN, Hilden, Germany), transferred into Pathogen Lysis tubes L (QIAGEN) and mechanically lysed by means of glass beads treating the samples according to the FastPrep protocol (QIAGEN). After addition of 40 µL Protease K, incubation at 56° C. for 30 min, 200 µL APL buffer were added and the samples were incubated at 70° C. for 10 min.

To isolate the non-animal nucleic acids by adsorption to a silica membrane, 200 µL ethanol (96-100%) were added to the sample and mixed by pulse-vortexing for 15 s. The sample was then applied onto a silica membrane suitable for nucleic acid binding, for example a silica membrane contained in the spin columns commercially available under the trademark name QIAamp or MinElute by QIAGEN, Hilden, Germany, and processed according to the manufacturer's protocol.

Example 1: Depletion of Human DNA from Blood Samples Spiked with *Bacillus subtilis*

1 mL human whole blood was spiked with $1\times10^6$ cells of *Bacillus subtilis* and processed according to the method of the invention as described in the above General Protocol A using a filter for separating the microbial cells.

For comparison, 200 µL of human whole blood were spiked with the same number ($1\times10^6$ cells) of *Bacillus subtilis* cells and processed using the commercially available QIAamp kit according to the manufacturer's protocol (QIAGEN, Hilden, Germany).

Figure 1:
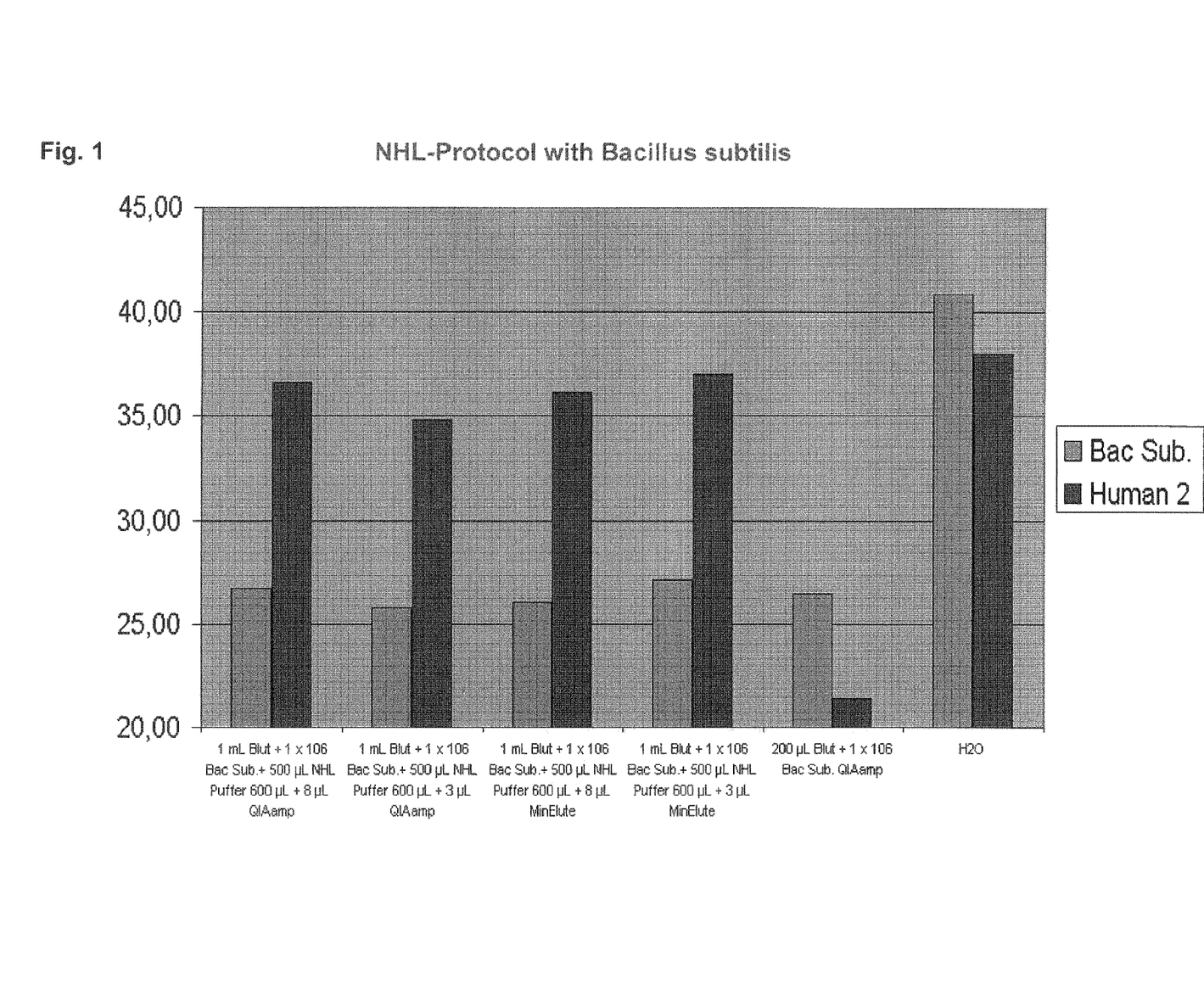
FIG. 1 shows the cycle threshold (CT) values obtained in real time polymerase chain reaction (rt-PCR) of nucleic acids isolated from blood samples which were first spiked with 1×10$^6$ cells of *Bacillus subtilis* and then processed either according to the method of the present invention (lanes 1 to 4) or the commercially available QIAamp kit (lane 5). In lane 6, the result obtained using water as non-target control (NTC) is shown (example 1).

The nucleic acids present in the eluate obtained at the end of each of the protocol were then amplified in rt-PCR. The obtained CT-values are shown in FIG. 1, lanes 1 to 4 representing samples processed according to the present invention while lane 5 represents the comparative sample processed using the QIAamp kit. In lane 6, water was used as a non-target control (NTC). In each lane on the left the ct values referring to the microbial nucleic acid is shown ("Bac Sub"), on the right the result referring to the human nucleic acid is shown ("Human 2").

Even though the initial amount of human DNA in the comparative sample was only ⅕ of the amount of human DNA in the sample processed according to the method of the present invention due to the smaller sample volume used in the comparative sample, the purified comparative sample comprises much more human DNA than the samples processed according to the method of the present invention. In the samples processed according to the method of the present invention on the other hand the amount of human DNA is close to the detection limit of rt-PCR. The amount of bacterial DNA is comparable for both methods.

The cycle threshold (CT) value is defined as the number of cycles required for the fluorescent signal detecting positive reaction in real time PCR to cross the threshold (background level). CT values are inversely proportional to the amount of target nucleic acid in the sample, so that a low CT value indicates a high amount of target nucleic acid in the sample and vice versa.

Example 2: WNA and WGA of DNA Isolated by the Method of the Present Invention for NGS Application Samples and comparative samples were prepared as described in Example 1. The obtained nucleic acids are then amplified by three PCR methods: rtPCR as in Example 1, whole genome amplification (WGA), or whole nucleic acid amplification (WNA). WGA was carried out using the REPLIg-Mini Kit of QIAGEN, Hilden, Germany according to the instructions.

Whole nucleic acid amplification is carried out by isolating the nucleic acids of the bacteria according to Example 1, carrying out a reverse transcription of the whole nucleic acids and thereafter making a WGA by using the REPLIg-Mini Kit of QIAGEN, Hilden, Germany according to the instructions.

Figure 2:
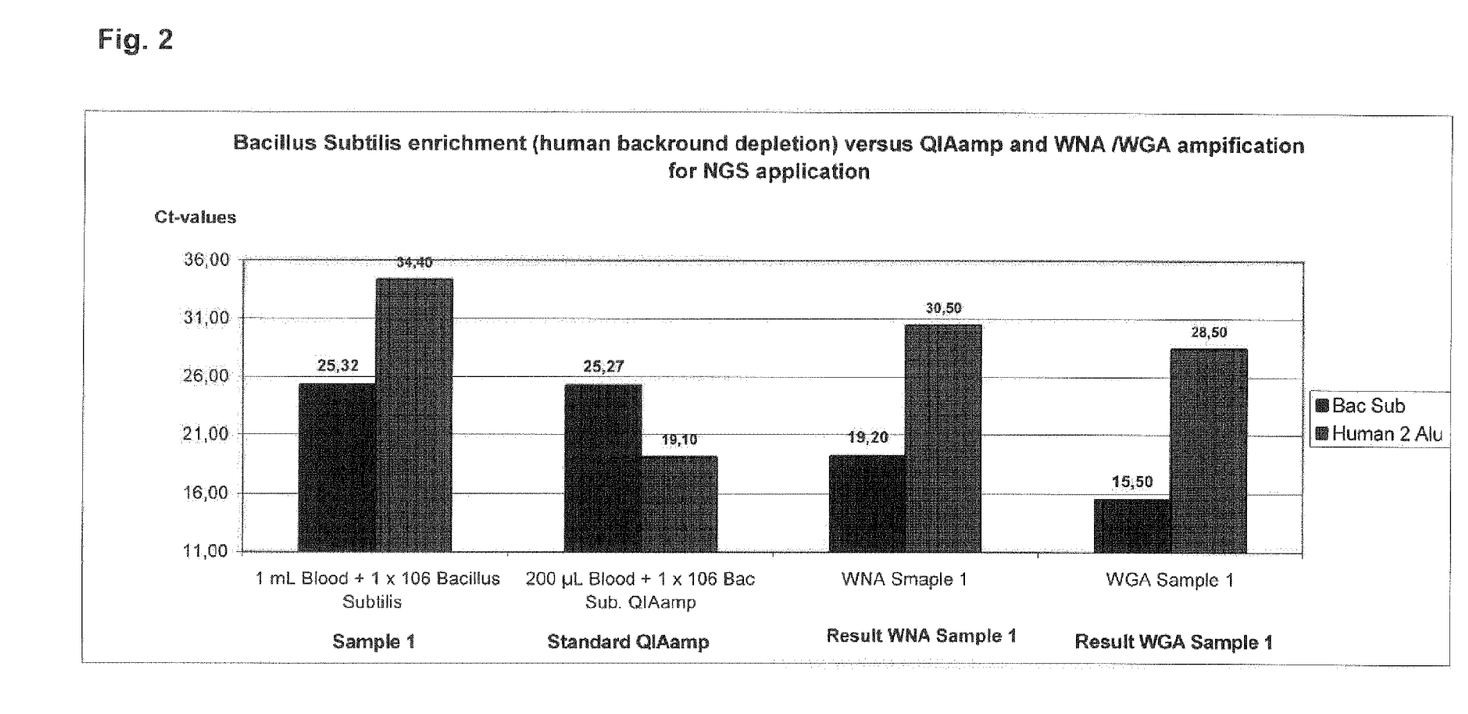
FIG. 2 shows the CT values obtained in rt-PCR (left and comparative example), after WNA and WGA, respectively, of a blood sample spiked with 1×10$^6$ cells of *Bacillus subtilis* processed according to the method of the present invention (example 2).

The results are shown in FIG. 2, showing the CT-values obtained. In each lane on the left ct values referring to the microbial nucleic acid is shown ("Bac Sub"), on the right the result referring to the human nucleic acid is shown ("Human 2"). This example demonstrates that non-animal nucleic acids isolated by the method of the present invention are suitable for amplification in WNA and WGA, respectively, and thus for next generation sequence (NGS) applications.

Example 3: Isolation of Bacterial DNA from Stabilized Blood Samples

Samples of human blood, each of them having a volume of 1 mL, were spiked with $1 \times 10^6$ cells of *Streptococcus haemolyticus* and supplemented with heparin, EDTA or citrate, respectively, as a stabilizer (in amounts as usual for blood conservation, i.e. heparin 17 IU/mL, EDTA 1.8 mg/mL, citrate 0.38%).

Samples stabilized with heparin, EDTA and citrate, respectively, were processed according to the method of the present invention as described in the above General Protocol immediately after spiking with the bacterial cells, while other samples were stored for 2 or 6 days, respectively, at room temperature or 4° C., respectively before being processed according to the above General Protocol A using a filter for separating the microbial cells.

The nucleic acids being present in the eluate obtained after carrying out of the above General Protocol A were amplified in rt-PCR.

Figure 3:
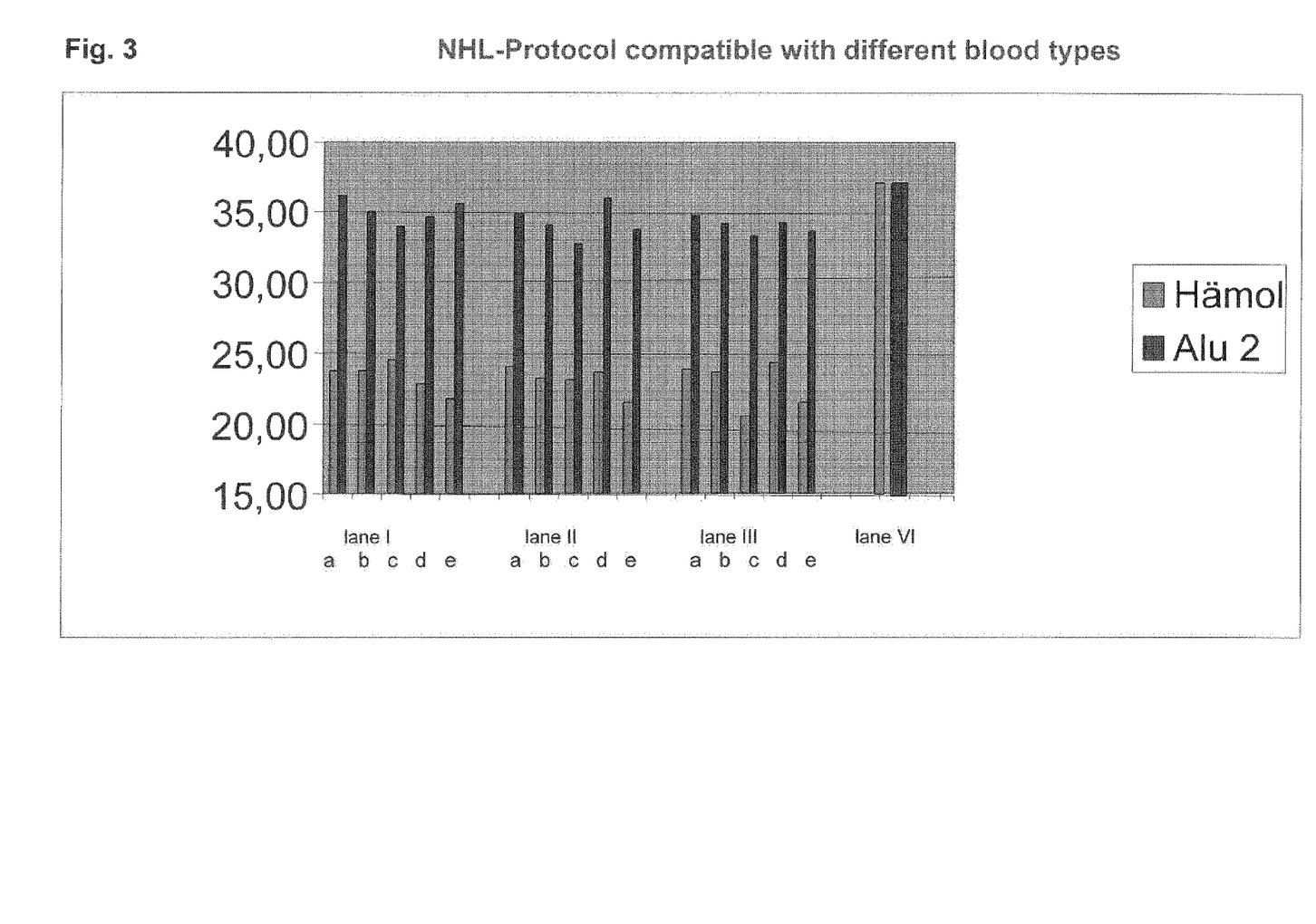

The results are presented in FIG. 3: FIG. 3 shows the CT values obtained in the rt-PCR (lanes I: heparin-stabilized samples; lanes II: EDTA-stabilized samples; lanes III: citrate-stabilized samples; lane IV: water as NTC). Samples shown in the respective lanes a) were processed according to the method of the present invention immediately after being collected and spiked with the bacterial cells. Samples shown in the respective lanes b) were stored at room temperature for two days before being processed. Samples shown in the respective lanes c) were stored at room temperature for six days before being processed. Samples shown in the respective lanes d) were stored at 4° C. for two days before being processed. Samples shown in the respective lanes e) were stored at 4° C. for six days before being processed. In each lane on the left the ct values referring to the microbial cells are shown ("Haemol"), on the right the result referring to the human nucleic acids is shown ("Alu 2").

These results demonstrate that the method of the present invention is useful for isolating non-animal nucleic acids from stabilized blood samples as well.

Example 4: Isolation of Bacterial DNA from Swabs

Samples were treated according to General protocol B. An amount of about $10^6$ *B. subtilis* cells were added to buccal swab samples in 1 mL PBS as described above and used for preparing the samples.

In a first approach the microbial cells are separated from the remainder of the samples after lysis of the human cells by a filtration step, in a second approach by centrifugation. The lysis of the human cells was carried out by lysis solution A, either comprising polyanethol sulfonic acid (+SPS) or being free of polyanethol sulfonic acid (−SPS), in any case with the aid of glass beads.

As a positive control the nucleic acids of $1 \times 10^6$ *B. subtilis* cells were isolated by using the QIAamp kit (QIAGEN, Hilden, German) according to the instructions. For comparison one of the samples (buccal swap, spiked with *B. subtilis*) was treated as well with the QIAamp kit (without prior lysis of the human cells). As a negative control (no target) served $H_2O$.

Figure 4:
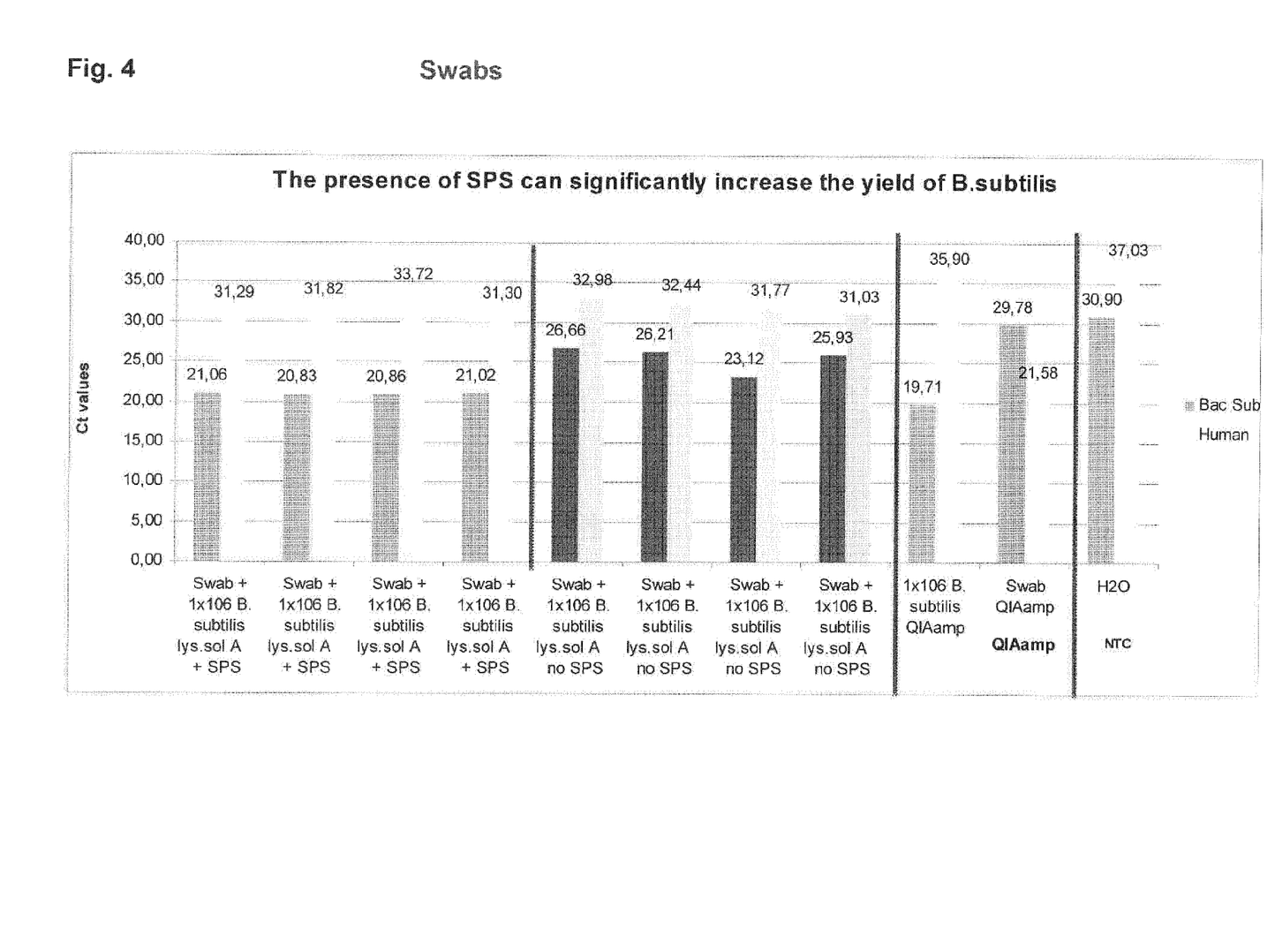
FIG. 4 shows the CT values obtained in rt-PCR of nucleic acids from buccal swab samples spiked with 10$^6$ cells of *Bacillus subtilis*, 4 samples each were treated with lysis solution A comprising polyanethol sulfonic acid sodium salt (SPS), or with lysis solution free of SPS and the microbial cells were separated by a filtration step (example 4).
Figure 5:
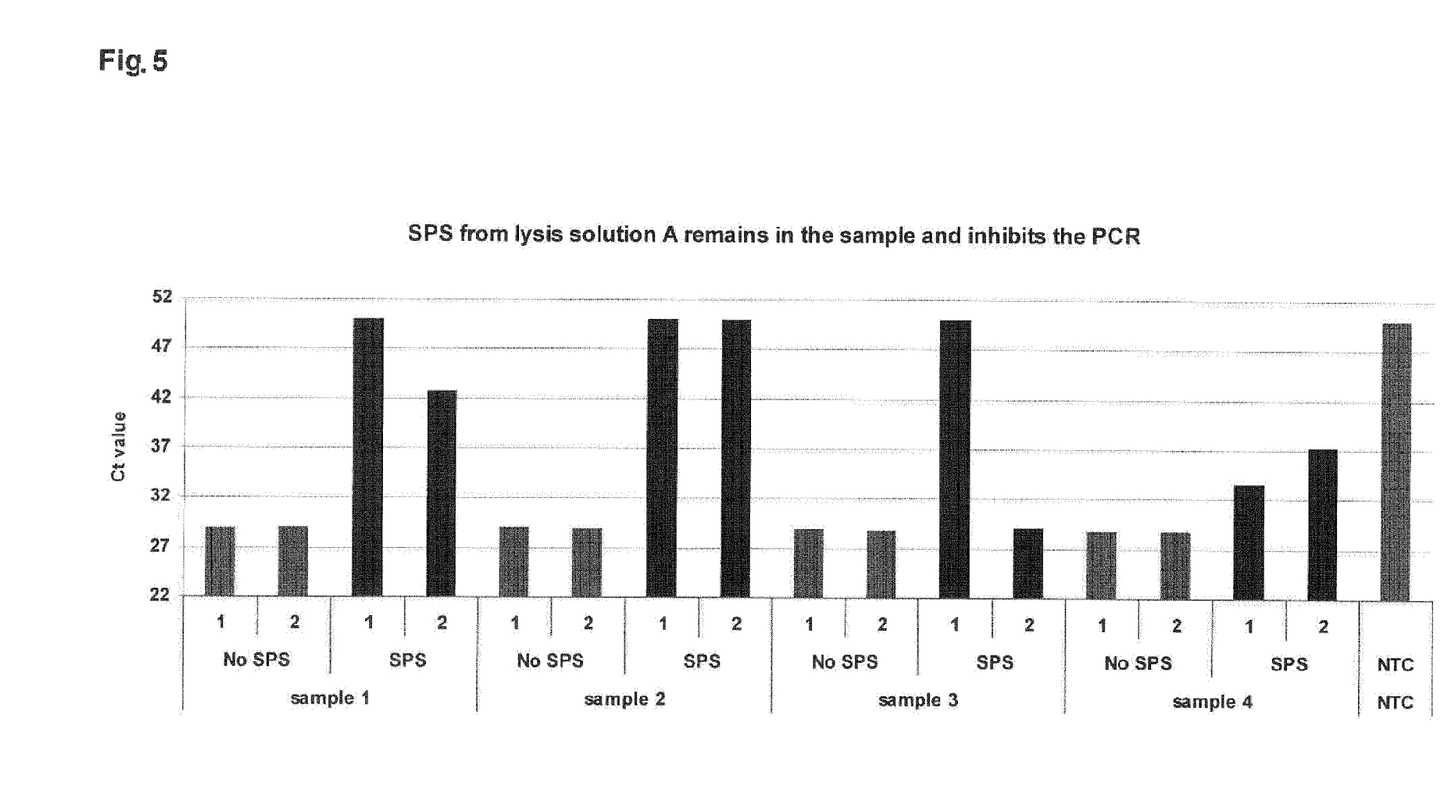
FIG. 5 shows the CT values obtained in rt-PCR of nucleic acids from four buccal swab samples spiked with 10$^6$ cells of *Bacillus subtilis*, the samples were treated with lysis solution A comprising polyanethol sulfonic acid sodium salt (SPS), or with lysis solution A free of SPS, respectively, and the microbial cells were separated by centrifugation (example 4). The lane on the right end represents the non-target control (last lane).

The nucleic acids being present in the eluate obtained after carrying out of the above General Protocol B or after treatment with the QIAamp kit were amplified in rt-PCR, the resulting CT-values are shown in FIGS. 4 and 5.

The samples shown in FIG. 4 were all treated by separating the microbial cells from the lysed human cell remainder by a filtration step. It can be seen, that the addition of SPS significantly increases the yield of *B. subtilis* nucleic acids from the samples.

The samples shown in FIG. 5 were treated by separating the microbial cells from the lysed human cell remainder by centrifugation. For each sample the rt-PCR was carried out (as a double check) twice with reference to *B. subtilis*. As can be seen, the CT values of the samples treated with the SPS comprising lysis solution have a high variation, due to the inhibition effect of SPS in the PCR. The lane on the right is the non target control (last lane).

Example 5: Next Generation Sequencing of DNA Obtained by the Method of the Present Invention The eluate obtained from samples, which were prepared according to General protocol A and the comparative method of example 1 were subjected to whole genome amplification by using the REPLI-g Mini Kit of QIAGEN according to the instructions of the Kit.

Figure 6:
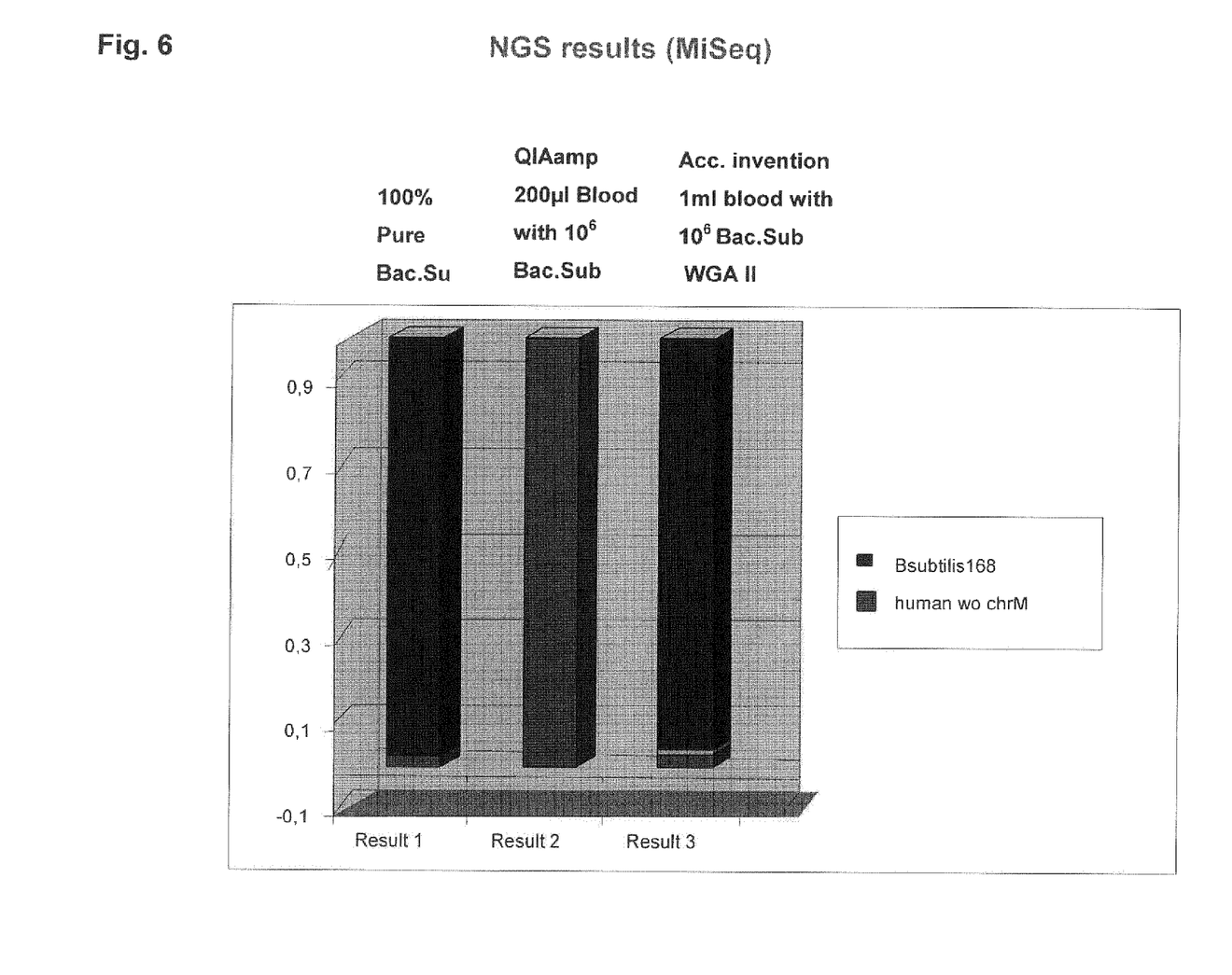
FIG. 6 shows the percentage of bacterial DNA (shown in black) and human DNA (shown in grey) obtained in Next Generation Sequencing from samples comprising virtually pure *Bacillus subtilis* DNA (lane 1), a blood sample spiked with 1×10$^6$ cells of *Bacillus subtilis* processed using the commercially available QIAamp kit (lane 2) and the method of the present invention (lane 3) (example 5).

The percentage of DNA matched against human and bacterial origin, respectively, for each sample is shown in FIG. 6. As a control, pure bacterial DNA from *Bacillus subtilis* was amplified and sequenced as described above, too (lane 1 in FIG. 5). Even in this control, small amounts of human DNA are detected, most probably due to environmental contamination. Comparing lane 2 (sample processed using the commercially available QIAamp kit) and lane 3 (sample processed according to the method of the present invention) it can be seen that by using the method of the present invention it is possible to amplify and sequence (almost) pure bacterial DNA, wherein the amount of human DNA hardly exceeds the usual environmental background.

The invention claimed is:

1. A method for selectively depleting animal nucleic acids from non-animal nucleic acids in a sample, the sample comprising animal cells and at least one further type of cells selected from microbial cells and plant cells or a combination thereof, the method comprising the steps of:
   i) selectively lysing the animal cells by contacting the sample with a lysis solution to obtain a mixture comprising intact microbial cells and/or plant cells as well as the animal nucleic acids released from the lysed animal cells into solution, said lysis solution being essentially chaotrope-free and comprising 0.01 to 15% (w/v) of a non-ionic surfactant, a water soluble salt selected from the group consisting of acetate, sulfate, glutamate, and mixtures thereof, and a sugar as a viscosity modifier,
   ii) digesting both DNA and RNA of the animal nucleic acids in the presence of the intact microbial and/or plant cells, and
   iii) separating the microbial and/or plant cells from the liquid part of the sample, including the digested animal nucleic acids.

2. The method according to claim 1, wherein in step ii) both DNA and RNA of the animal nucleic acids are digested in one step.

3. The method according to claim 1, wherein in step ii) both DNA and RNA of the animal nucleic acids are digested in one step with an endonuclease that degrades both DNA and RNA.

4. The method according to claim 1, wherein the nonionic surfactant is selected from the group consisting of a sorbitan ester of fatty acids, a polyoxyethylene sorbitan ester of fatty acids, a polyoxyalkylene ether of fatty alcohols, a polyoxyalkylene etherof alkylphenols, a poloxamer, a saponin, or a mixture of any thereof.

5. The method according to claim 1, wherein the sugar is glucose or sucrose.

6. The method according to claim 1, wherein the lysis solution further comprises a polyanionic sulfonate.

7. The method according to claim 1, wherein the animal cells comprise mammalian cells, and/or wherein the further cells comprise microbial cells that are bacterial cells, archae cells, fungal cells, or any combination thereof, and/or wherein the sample comprises a tissue, tissue homogenate, cell culture, bone marrow aspirate, bone homogenate, swab, swab rinsate, or body fluid.

8. The method according to claim 7, wherein the body fluid is amniotic fluid, aqueous humour, bile, bladder lavage, blood, breast exudates, bronchoalveolar lavage, cerebrospinal fluid, chyle, chyme, cytosol, feces, gastric contents, in particular gastric acid, interstitial fluid, joint fluid, lymph, menses, mucus, plasma, pleural fluid, pus, saliva, sebum, semen, serum, sputum, sweat, synovial fluid, tears, urine, vaginal secretions, or vitreous humour.

9. The method according to claim 1, further comprising the steps of:
   i) removing a liquid part of the sample from the remaining cells, and/or
   ii) removing and/or inactivating any nuclease present along with the remaining cells.

10. The method according to claim 9, wherein removing and/or inactivating any nuclease present along with the remaining cells comprises digesting the nuclease with a proteinase.

11. The method according to claim 1, further comprising after step iii), analyzing the microbial and/or plant cells or any parts thereof.

12. The method according to claim 11, wherein analyzing the microbial and/or plant cells or any parts thereof comprises culturing, cytometry, microscopy, immunodetecting, and/or lysing the microbial or plant cells; and/or concentrating, isolating, purifying, amplifying and/or analyzing the microbial and/or plant nucleic acids.

13. The method according to claim 1, wherein step iii) comprises separating the microbial cells or plant cells by centrifugation.

14. The method according to any claim 1, wherein step iii) comprises filtering the sample through a solid filter to retain the microbial and/or plant cells as retentate on the filter while a liquid part of the sample, including the digested animal nucleic acids, passes the filter as a filtrate.

15. The method according to claim 14, wherein the solid filter fulfills at least one of the following conditions:
   i) the filter comprises at least one part having a pore size being in the range of 0.1-1.5 µM;
   ii) the filter comprises polyester, polyethersulfone (PES), cellulose, cellulose acetate (CA), mixed cellulose esters (MCE), polytetrafluoroethylene (PTFE), polyamide (PA), Nylon, polypropylene (PP), ceramics, glass fibers, silica, or any combination or mixture thereof.

\* \* \* \* \*